(12) United States Patent
Zampollo et al.

(10) Patent No.: US 12,138,197 B2
(45) Date of Patent: Nov. 12, 2024

(54) ABSORBENT MAT WITH PERIMETER SEAL

(71) Applicant: R. SABEE COMPANY, LLC, Appleton, WI (US)

(72) Inventors: Fabio Zampollo, Crema (IT); Ivano Gagliardi, Pescara (IT); Anthony Donovan, Appleton, WI (US)

(73) Assignee: R. SABEE COMPANY, LLC, Appleton, WI (US)

( * ) Notice: Subject to any disclaimer, the term of this patent is extended or adjusted under 35 U.S.C. 154(b) by 0 days.

(21) Appl. No.: 16/348,348

(22) PCT Filed: Nov. 9, 2017

(86) PCT No.: PCT/EP2017/078688
§ 371 (c)(1),
(2) Date: May 8, 2019

(87) PCT Pub. No.: WO2018/087197
PCT Pub. Date: May 17, 2018

(65) Prior Publication Data
US 2019/0262168 A1    Aug. 29, 2019

(30) Foreign Application Priority Data
Nov. 9, 2016 (GB) .................................... 1618903

(51) Int. Cl.
*A61F 5/48* (2006.01)
*A61F 13/53* (2006.01)
(Continued)

(52) U.S. Cl.
CPC .......... *A61F 5/485* (2013.01); *A61F 13/5323* (2013.01); *B32B 5/26* (2013.01);
(Continued)

(58) Field of Classification Search
CPC .................. A61F 5/485; A61F 13/5323; A61F 2013/53054; A61F 13/15739;
(Continued)

(56) References Cited

U.S. PATENT DOCUMENTS 3,871,037 A * 3/1975 Willington ........ A61F 13/51305
5/500
3,888,257 A * 6/1975 Cook .................. A61F 13/5323
604/368

(Continued)

FOREIGN PATENT DOCUMENTS

| JP | 2005137617 | 6/2005 | | |
|---|---|---|---|---|
| WO | WO-2006039188 A2 | * | 4/2006 | ....... A61F 13/15658 |
| WO | WO-2016207444 A1 | * | 12/2016 | ....... A61F 13/15577 |

OTHER PUBLICATIONS

"Adhesive." Collins-Dicitonary, Collins, www.collinsdictionary.com/us/dictionary/english/adhesive.*

(Continued)

*Primary Examiner* — David R Hare
*Assistant Examiner* — Madison Emanski
(74) *Attorney, Agent, or Firm* — RYAN KROMHOLZ & MANION, S.C.

(57) ABSTRACT

The present invention is an absorbent mat, such as a bed pad or a change mat, e.g. for protecting an underlying support from soiling, with a perimeter seal to prevent side-way leakage, as well as method for the formation of such a pad or mat.

14 Claims, 4 Drawing Sheets

(51) Int. Cl.
*A61F 13/532* (2006.01)
*B32B 5/26* (2006.01)
*B32B 29/02* (2006.01)
*B32B 37/06* (2006.01)
*B32B 37/12* (2006.01)

(52) U.S. Cl.
CPC .............. *B32B 29/02* (2013.01); *B32B 37/06* (2013.01); *B32B 37/12* (2013.01); *A61F 2013/53054* (2013.01); *B32B 2262/04* (2013.01); *B32B 2307/726* (2013.01)

(58) Field of Classification Search
CPC .......... A61F 13/539; A61F 2013/15056; A61F 2013/15869; A61F 2013/15878; A61F 2013/1591; A61F 2013/530343; A61F 2013/530496; A61F 2013/53908; A61F 2013/53991; A61F 13/15658; A61F 13/534; A61F 13/4942; A61F 13/53418; A61F 13/53427; A61F 13/537; A61F 2013/530532; A61F 13/15577; A61F 13/15699; A61F 13/15731; A61F 13/15747; A61F 13/49017; A61F 13/532; A61F 13/53436; A61F 13/535; A61F 13/538; A61F 13/8405; A61F 2013/49038; A61F 2013/530489; A61F 2013/530547; A61F 2013/530554; A61F 2013/530569; A61F 2013/530591; A61F 2013/5307; A61F 2013/5315; A61F 2013/53472; A61F 2013/5349; B32B 5/26; B32B 29/02; B32B 37/06; B32B 37/12; B32B 2262/00; B32B 2307/726; B32B 2262/04; Y10T 442/60
USPC .................................. 428/192, 193; 3/2; 5/22
See application file for complete search history.

(56) References Cited

U.S. PATENT DOCUMENTS

| | | | | |
|---|---|---|---|---|
| 4,176,667 | A * | 12/1979 | Herring | A61F 13/15699 604/368 |
| 4,232,674 | A * | 11/1980 | Melican | A61F 13/206 604/369 |
| 4,551,144 | A * | 11/1985 | Graber | A61F 5/4401 604/378 |
| 4,886,697 | A | 12/1989 | Perdelwitz, Jr. | |
| 5,252,374 | A * | 10/1993 | Larsonneur | A61F 5/485 428/77 |
| 5,476,456 | A | 12/1995 | Rankin et al. | |
| 5,701,617 | A * | 12/1997 | Colby | A47C 27/006 5/484 |
| 6,911,407 | B2 * | 6/2005 | Sherrod | A47C 27/006 442/101 |
| 9,271,473 | B2 * | 3/2016 | Ryu | A01K 1/0152 |
| 2003/0124928 | A1 | 7/2003 | Sherrod | |
| 2013/0115437 | A1* | 5/2013 | Johnston | C09J 7/29 428/220 |
| 2013/0260978 | A1* | 10/2013 | Tombuelt-Meyer | A61F 13/15804 493/379 |
| 2014/0163502 | A1* | 6/2014 | Arizti | A61F 13/4942 604/366 |

OTHER PUBLICATIONS

Search Report dated Jan. 25, 2018 in International Application Serial No. PCT/EP2017/078688.
Written Opinion dated Jan. 25, 2018 in International Application Serial No. PCT/EP2017/078688.

* cited by examiner

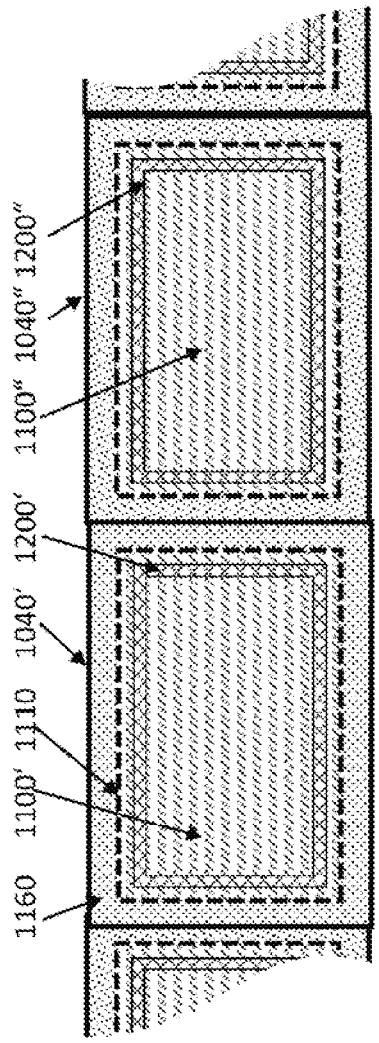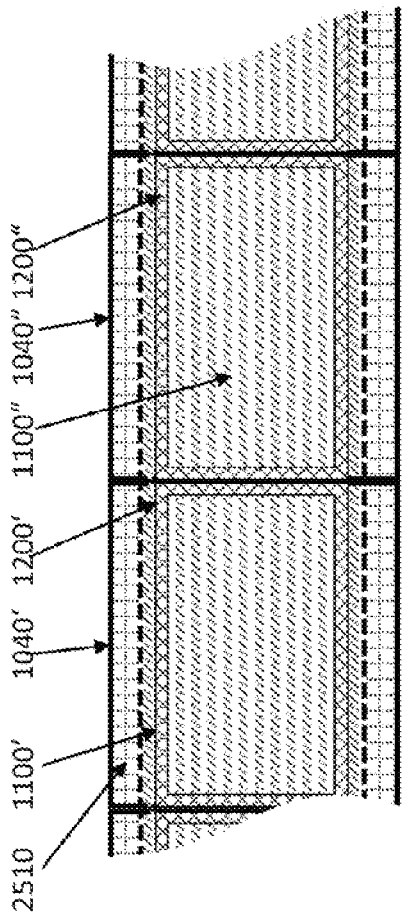

ABSORBENT MAT WITH PERIMETER SEAL

FIELD OF THE INVENTION

The present invention is an absorbent mat, such as a bed pad or a change mat, e.g. for protecting an underlying support from soiling, as well as method for the formation of such a pad or mat.

BACKGROUND

Mats or pads to prevent soiling of a support on which such mats are placed, are well known in the art, see e.g. U.S. Pat. No. 4,097,943 describing an underpad for a bed comprising an absorbent layer, which is enveloped between a liquid permeable and an impermeable layer, or WO20060431151 describing a baby changing mat.

Side seals for preventing sideway leakage in absorbent articles are quite widely known, e.g. from WO1994020002A1, generally describing the sealing at an outer rim of an absorbent article. GB1207352A describes that the edges of a multi-ply product can be sealed by an innocuous adhesive or heatsealable polymer. In U.S. Pat. No. 3,871,037A, the overfolding of a bottom impermeable layer such as polythene around all four sides for preventing lateral leakage is described.

However, such side seals have been found to be inefficient in case of consecutive loadings exceeding the liquid acquisition ability and/or ultimate liquid storage capacity of the main absorbent layer.

Another approach has been to employ gelling material for sealing purposes in other application areas. Thus, WO1996023024A1 discloses the use of gellable material as sheathing material in the cable industry to induce so-called water-blocking, which aims at preventing water penetrating to the core of the cable in transverse as well as longitudinal direction. Suitable compounds were described as petrojelly-like compounds or substrate materials coated with a superabsorbent powder. In US20040215118A, a disposable, water resistant surgical bandage or cast cover is described, which comprises powder ring capable of gelling when moistened and disposed adjacent each opening during use.

However, these approaches were not in the context of a disposable absorbent pad or mat, where not only the sealing properties are relevant but also the overall absorbency properties and the health and skin care benefits of a user, i.e. a person resting on a mat, and there is still a need for absorbent mats with improved liquid handling capability.

The present invention addresses this by a dual functionality of a perimeter seal for preventing sideway (i.e. longitudinal (x-) and lateral (y-)directionally) liquid leakage: the first amounts of x-y-directional liquid flow reaching the seal are absorbed by the superabsorbent material in the perimeter seal, upon which this material swells, thereby forming a dam against further x-y-flow of subsequent liquid flows.

SUMMARY

In a first aspect, the present invention is a disposable absorbent mat, which can be described in Cartesian coordinates with
- a first extension in the x-direction, corresponding to the length of the mat and defining generally x-directionally extending mat margins;
- a second extension, in the y-direction, corresponding to width of the mat, preferably being shorter the first extension, and defining generally cross-directionally extending mat margins; and
- a third extension, in the z-direction, corresponding to the thickness of the mat, perpendicular to the first and the second extensions, and significantly smaller than the first and the second extension.

The absorbent mat comprises in a z-directional arrangement
- a first surface of a first cover web adapted for being oriented towards a user during the intended use;
- a second surface of a second cover web, opposite the first surface and adapted for being oriented towards a support during the intended use; and
- an absorbent core there between, which comprises fibrous, preferably cellulosic material, and optionally SAP material at an essentially x-y-directional homogeneous distribution, and
- optionally at least one core carrier web material, preferably a paper tissue material.

The first and the second cover web extend longitudinally and laterally outwardly of the absorbent core, thereby forming a mat perimeter between the mat margins and the absorbent core x- and y-directionally, and are connected to each other in this mat perimeter, The absorbent mat further comprises a perimeter seal, which is positioned along essentially closed line within the x-y-extending margins of the absorbent mat essentially closed perimeter seal line, and exhibits a perimeter seal width extending perpendicular to the perimeter seal line of at least 5 mm, preferably more than 10 mm and less than 40 mm, preferably less than 30 mm.

The absorbent mat further comprises in the perimeter seal superabsorbent polymer (SAP) material, at a local BW-concentration of at least 60% of the combined basis weight of core fibers, such as cellulose, SAP, and carrier (if present).

The absorbent mat may further exhibit one or more of the features selected from the group consisting of:
i) The perimeter seal width is essentially constant along the perimeter seal line;
ii) The SAP is applied to the perimeter seal at a local basis weight of more than 25 g/m², preferably more than 100 g/m², even more preferably more than 300 g/m²;
iii) The SAP is applied to the perimeter seal at a local basis weight that is at least 1.05, preferably more than 1.10 as high as the basis weight of the SAP in the absorbent core, if present;
iv) The local BW-concentration in the perimeter seal is essentially constant along the perimeter seal line;
v) The absorbent core comprises SAP material at a basis weight of less than about 300 g/m² preferably less than 100 g/m², more preferably less than 50 g/m², including essentially zero, whereby the SAP material is either essentially homogeneously distributed in a x-y-plane, or the basis weight of the SAP material is an average of the area encircled by the perimeter seal line;
vi) The perimeter seal comprises SAP material which exhibits an SFC-value of less than about $40 \times 10^{-7}$ cm³ sec/g;
vii) The absorbent core extends laterally or longitudinally outwardly of the perimeter seal;
viii) The perimeter seal follows essentially the shape of the mat perimeter;
ix) The distance between the perimeter seal and the mat perimeter is, when measured perpendicularly to the perimeter seal line, less than about 100 mm, preferably less than 50 mm, including being essentially zero;
ix) The perimeter seal line has an oval or a rectangular shape, the latter optionally with rounded corners.

In another aspect, the present invention is a method for the manufacture of an absorbent mat, which can be described in Cartesian coordinates with a first extension in the x-direction, corresponding to the length of the mat and corresponding to the machine direction of the manufacturing method;

a second extension in the y-direction, corresponding to width of the mat, preferably being shorter the first extension and corresponding to the cross-machine direction of the manufacturing method; and a third extension, z-direction or thickness, perpendicular to the first and the second extensions, and significantly smaller than the first and the second extension.

The absorbent mat comprises z-directionally a first surface of a first cover web adapted for being oriented towards a user during the intended use;

a second surface of a second cover web, opposite the first surface and adapted for being oriented towards a support during the intended use; and an absorbent core there between, exhibiting an absorbent core margin and an x-y-extension smaller than the x-y-extension of the mat, and comprising fibrous, preferably cellulosic material and optionally superabsorbent polymer (SAP).

The first and the second cover web extend longitudinally and laterally outwardly of the absorbent core, thereby forming a mat perimeter circumscribing the core x- and y-directionally, and being connected to each other in the perimeter.

The absorbent mat may optionally comprise at least one core wrap material.

The absorbent mat further comprises a perimeter seal, which exhibits a perimeter seal width extending perpendicular to a perimeter seal line of at least 5 mm, preferably more than 10 mm and less than 40 mm, preferably less than 30 mm. The perimeter seal line is positioned along an essentially closed perimeter seal line-and comprises superabsorbent material, at a local basis weight concentration of at least 60% of the combined basis weight of fibrous material, such as cellulose, SAP, and core carrier, if present.

The method according to the present invention comprises the steps of a) providing
  a1) a first and a second cover web material from a web supply unit, respectively;
  a2) an absorbent core making unit, selected from a fiber, preferably cellulosic fiber, lay-down unit for individualizing fibers and forming a web of fibers, and/or a core web unwinding unit;
  a3) optionally a core wrap supply unit, preferably a tissue unwind unit;
  a4) at least one superabsorbent polymer (SAP) material supply and application unit;
  a5) at least one connecting unit;
b) making an absorbent core by using the core making unit and optionally a SAP material supply and application unit;
c) forming a perimeter seal before, during, or after making of the absorbent core such that the perimeter seal is exhibiting a perimeter seal width extending perpendicular to the perimeter seal line of at least 5 mm, preferably more than 10 mm and less than 40 mm, preferably less than 30 mm, whereby the perimeter seal is positioned along an essentially closed perimeter seal line; and comprises superabsorbent material at a local basis weight concentration of at least 60% of the combined basis weight of fibrous material, such as cellulose, SAP, and core carrier, if present;

d) enveloping the absorbent core and the perimeter seal between the first and the second cover web;

e) connecting the cover webs at least in the mat perimeter outwardly of the perimeter seal, as well as optionally the core wrap materials to the absorbent core and optionally the core wrap material(s) to the cover webs.

The perimeter seal may be formed by SAP printing, preferably without simultaneously applying other fibrous material, such as pulp fibers, to the perimeter seal.

The connecting in step e) may be performed by glue application, preferably spray glue application or melt fusion bonding, preferably ultrasonic bonding.

BRIEF DESCRIPTION OF THE FIGURES

FIGS. 4A and B depict particular executions according to the present invention.

Same numerals in different figures refer to same or equivalent features or elements. The figures are schematic and not necessarily to scale.

DETAILED DESCRIPTION

Figure 1:
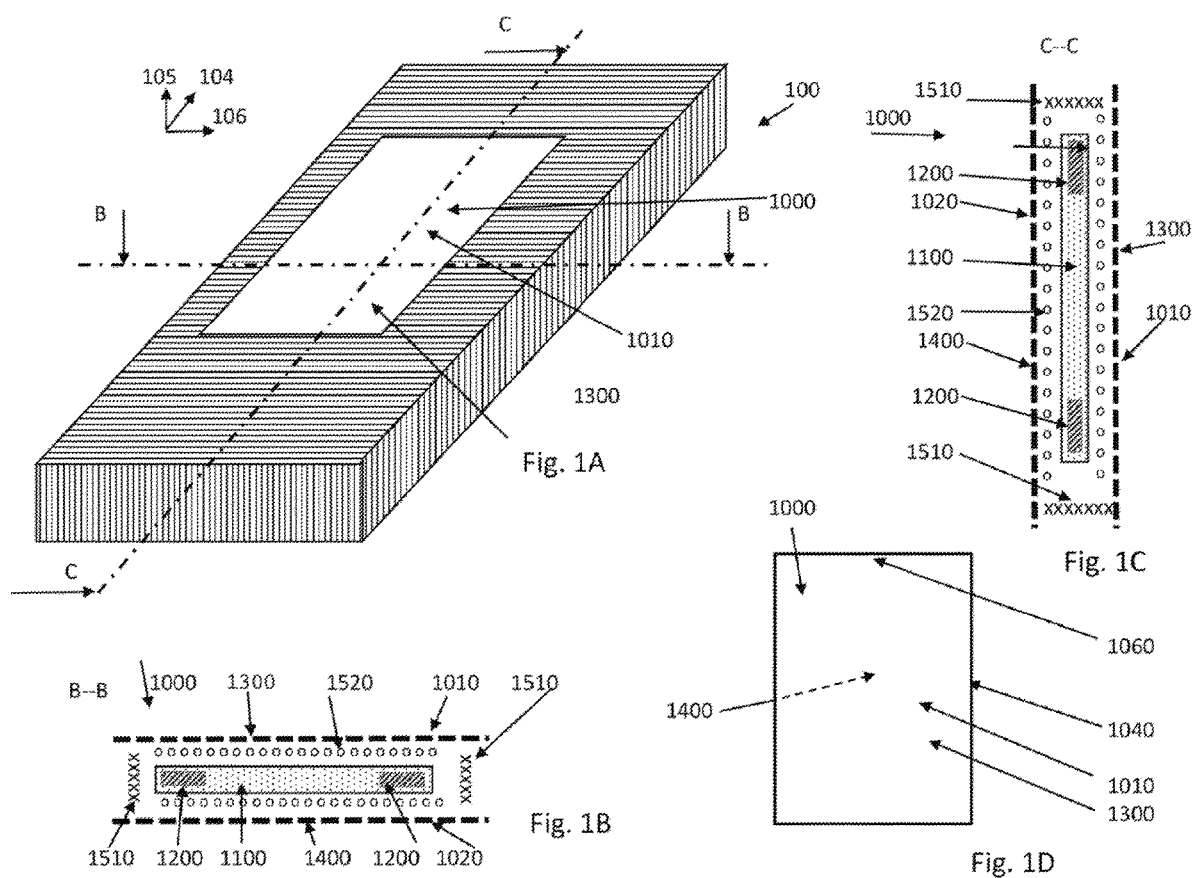
FIG. 1A to D depict an absorbent mat according to the present invention.

In a first aspect, the present invention is a disposable absorbent mat or pad, in a second aspect, the present invention relates to the making of such an article.

The term "absorbent mat" is often also used interchangeably with the term "absorbent pad" and refers to a generally flat structure, though not necessarily with an even thickness, that is adapted to absorb liquid and that may prevent a support on which such a mat is positioned from getting soiled or wetted. An absorbent mat may be used as a bed pad for preventing soiling on a mattress or other bedding items like bed sheets or fitted sheets from bodily exudates of a person positioned there on, such as when the person is not wearing other protective clothing like a diaper, or when such clothing is overloaded or poorly fitting so as to leak at receipt of the bodily exudates of the wearer, as can be without any limitation any of faeces, urine, menses, wound secrets, but also saliva, or sweat. However, also an inverse scenario is considered to be within the present context, such as when a baby change mat is put on a ground to protect the baby from being soiled during diaper changes Within the present context, reference is made to a Cartesian coordinate system wherein the absorbent mat is exhibiting a length, longitudinal or x-direction, a width, cross-directional or y-direction and a thickness or z-direction perpendicular thereto. In the x-y-plane, the absorbent mat comprises an absorbent mat perimeter.

When the absorbent mat is put on a support which is typically described by length and width, such as a bed or a mattress of a bed, the x-, y-, and consequently also z-direction of the absorbent mat will be understood to be aligned with this direction. Typically, the manufacturing direction for such an article will be that the machine direction of the process or equipment is aligned with length direction of the article, in particular of the absorbent core.

When the support onto which an absorbent mat according to the present invention is placed has less clearly defined length and width orientation, such as when considering a baby change mat that may be placed on a table or even on the ground, the term length or longitudinal refers to the direction that the article had during its manufacture and that a skilled person will be readily able to determine such as from material properties or other material application characteristics, such as glue beads.

The term "disposable" as used herein means when referring to an absorbent mat that it is intended to be discarded in an environmentally considerate manner after use, which may be a single use or may be several uses such as when during the first use no or no substantial soiling is occurring. Thus, the present invention is not directed towards mats or parts thereof that are re-usable, e.g. by washing or laundering.

The terms "comprise," "comprising," and "comprises" are open ended terms, each specifying the presence of the feature that follows, e.g. a component, but does not preclude the presence of other features, e.g. elements, steps, components known in the art or disclosed herein. The words "typically", "normally", "advantageously" and the likes also qualify features which are not intended to limit the scope of the claims unless specifically indicated to do so.

Unless expressly mentioned otherwise, all percentages (%) refer to weight based percentages. The term "basis weight concentration" refers to the percentage ratio of the weight of a particular material relative to the total amount of materials in a given x-y-extending area. The term "local" such as in the context of basis weights refers to a unit area, and may be a calculated value, such as from known or given basis weights of layers in the respective region, or may be a measured value by extracting individual elements in a unit area, which should cover the respective region but for practical reasons of the measurement should not be lower than 5 mm by 5 mm.

An absorbent mat according to the present invention comprises an absorbent core structure as well as a liquid permeable cover- or topsheet intended to be oriented towards a user during use, a liquid impermeable backsheet opposite to the topsheet, and at its perimeter a liquid flow barrier or seal.

The absorbent mat may have an overall length of from about 500 mm to about 1000 and in the manufacturing configuration, i.e. unfolded, an overall width of from about 500 mm to about 1000 mm. It may exhibit a thickness of from about 0.5 mm to about 10 mm or more. In a particular execution, the absorbent mat has a rectangular shape optionally with rounded corners.

An absorbent mat comprises an absorbent core, exhibiting an absorbent core shape with an absorbent core perimeter, which may be distanced from or coinciding with the absorbent mat perimeter, or partly being distanced and partly coinciding. The absorbent core may comprise various absorbent materials as well known in the art, such as woven material, non-woven material, airlaid material that may comprise absorbent fibers such as particularly preferred cellulosic fibers or absorbent man-made fibers, or binder fibers, but also particulate material such as without limitation so called well known superabsorbent polymer (SAP) materials. The term "absorbent" refers to the capability of receive and preferably retain liquids, often aqueous body exudates, within voids of the structure, such as in inter-fiber interstices, or within the materials, such as in cellulosic fibers upon swelling, or in the SAP-network. The absorbent core preferably has sufficient internal structural integrity and strength so as to withstand the foreseeable manufacturing conditions. Preferably, the structural integrity of the absorbent core is not negatively affected by moisture. The absorbent core may be a layered structure comprising two or more sub-layers of the same or different design or materials.

The absorbent core may comprise SAP material, as may be positioned between sublayers of the absorbent core and/or mixed homogeneously or inhomogeneously with fibers, preferably cellulose pulp fibers, of a single absorbent core layer, of one sublayer, or of more than one sub-layer.

The absorbent core structure of the absorbent mat may exhibit a basis weight of from about 40 $g/m^2$ to about 600 $g/m^2$; as may be determined according to EDANA NWSP 130.1R0, or equivalent.

If the absorbent core structure comprises SAP material, it preferably does so at a basis weight of less than about 300 $g/m^2$ preferably less than 150 $g/m^2$, more preferably less than 100 $g/m^2$, including essentially zero, whereby said SAP material is either essentially homogeneously distributed in a x-y-plane, or said basis weight of said SAP material is an average of the area encircled by the inwardly positioned margin of the perimeter seal line. The SAP material may be of a conventional type and quality, and may exhibit absorbent capacities of more than 20 mug, preferably more than 30 ml/g, when determined according to the "centrifuge retention capacity" method, EDANA NWSP 241.0R2.

Preferably the SAP material in the absorbent core does not impede the x-y-directional fluid transport, and thus gel-blocking should be avoided such as by preferably using SAP materials exhibiting relatively higher permeability performance, such as by exhibiting "saline flow conductivity" (SFC) values more than $20 \times 10^{-7}$ $cm^3$ sec/g, or more than $60 \times 10^{-7}$ $cm^3$ sec/g, but typically do not exceed $600 \times 10^{-7}$ $cm^3$ sec/g, whereby SFC refers to saline flow conductivity as may be determined according to the method as described in detail in U.S. Pat. No. 5,599,335, to which express reference is made for this test method.

The SAP material may exhibit a relatively slow liquid acquisition performance so as to allow better distribution of the liquid in the x-y-direction before being "locked" away in the SAP material.

This x-y-directional distribution may also be enhanced by applying the SAP material at relatively low local concentrations of less than 60% or even less than 40%, or low local basis weights, such as less than 120 $g/m^2$, often less than 80 $g/m^2$ or even less than 60 $g/m^2$. The absorbent core may exhibit an improved integrity by being embossed or calendered, preferably under a high pressure of e.g. 50 N/mm of calendering line or even 100 N/mm or more. Optionally, the effect of the embossing may be further enhanced by increasing the moisture content of at least a portion of the cellulosic material in the absorbent core.

The absorbent material of the absorbent core may be combined with one or more core carrier materials. For example, lose fibers may be laid onto a carrier web material, such as a paper tissue e.g. exhibiting a basis weight of between 15 $g/m^2$ to 25 $g/m^2$ or a nonwoven web material, e.g. a web comprising melt-blown and spunbonding layers.

A second carrier material may be positioned opposite of the first core carrier material.

The core cover material may exhibit the same dimensions as the absorbent core, though an execution is included, where the core cover materials extends laterally beyond the longitudinally extending margins of the absorbent core, for example by at least 5 mm or even 10 mm or more.

The absorbent article according to the present invention comprises cover materials for enveloping the absorbent core and the core carrier materials, if present.

A first cover, as may be oriented towards a user of the article, who may rest thereon, and henceforth often referred to as topsheet, is a liquid permeable material, such as apertured film materials or "nonwoven web" materials, i.e. manufactured material, web, sheet or batt of directionally or randomly oriented fibers, bonded by friction, and/or cohesion and/or adhesion, excluding paper and products which are woven, knitted, tufted, stitch-bonded, incorporating binding yarns or filaments, or felted by wet milling, whether or not additionally needled. The fibers may be of natural or man-made origin. Without intending any limitation, such non-woven materials may be made by processes as well known in the art, and from a strength point of view are preferably of the spunbonded type, optionally combined with meltblown layers. The total basis weights of a topsheet material may be more than about 5 g/m², though often the basis weight will be more than 10 g/m² and for certain applications requiring good strength properties even more than 20 g/m², as may be determined according to EDANA NWSP 130.1R0 or equivalent. For softness and cost reasons, the topsheet materials exhibit typically a basis weight of less than 100 g/m², preferably less than 50 g/m² or even less than 30 g/m².

A second cover is positioned opposite of the first cover, which may be oriented towards a support structure or surface, and which are also referred to a backsheet material. Typically, such a second cover is a liquid impermeable material, and may comprise or essentially consist of film materials, such as polyethylene or polypropylene films, optionally further comprising fibrous materials, such as when being laminated with a nonwoven material to provide a so called cloth-like material. Typically such materials exhibit good softness and may exhibit basis weights of below about 10 g/m², though often the basis weight ranges between 10 g/m² and 20 g/m², and higher basis weights even over 30 g/m² may be employed, for example when an increased mechanical strength is required.

The first and the second cover envelop the absorbent core and the core carrier, if present, by being at least connected along the perimeter of the mat. The connecting may be achieved by conventional means, such as applying adhesives in a spray, slot coating or bead application. The connecting can also be achieved by melt fusion bonding, such as by heat sealing or heat or pressure bonding or ultra-sonic bonding.

It is a particular feature of the present invention that the article comprises a perimeter seal for reducing or even preventing leakage of liquids sideways, either laterally or longitudinally. To this end, a perimeter seal is applied to the article to essentially fully frame the article along the periphery of the absorbent mat. The refers to a design, where the perimeter seal generally follows the contours of the absorbent mat, with the outward margin of the perimeter seal being distanced to the margin of the absorbent mat by more than 5 mm, more than 10 mm, often between 20 mm and 40 mm, though preferably less than 100 mm, or less than 60 mm Thus in the particular execution of a rectangular shape of the absorbent mat, the outer margin of the perimeter seal also has a rectangular shape of a smaller rectangle. The distance of the perimeter seal margin to the margin of the absorbent mat may be constant throughout the absorbent mat, or it may vary e.g. by being different along the longitudinal margins as compared to the cross-directional margins, or by being not parallel to the margin of the mat. For a particular execution, the distance may be essentially zero along the cross-directionally extending margins of the absorbent mat, whilst being larger along the longitudinally extending margins.

The perimeter seal is positioned along a perimeter seal line, which essentially forms a closed line within the perimeter of the absorbent mat. The term "essentially forming a closed line" refers to a design of the perimeter seal forming a closed line, which, however, may be in the form of a dotted line or a dash-dotted line, i.e. may have single or multiple interruptions which are so small, that they essentially do not hinder the liquid barrier properties of the perimeter seal. The perimeter seal may exhibit a constant perimeter seal width along the perimeter seal line, which extends essentially perpendicular to the perimeter seal line. However, the perimeter seal line width may vary, such as when the line width is smaller or wider along the longitudinally extending margins of the absorbent mat as compared to the line width along the cross-directionally extending margins.

The perimeter seal comprises SAP material. In order to provide the fluid barrier properties, there should be sufficient absorbency. The amount of the SAP material in the perimeter seal is preferably at least 25 g/m² of local BW weight (i.e. just considering the perimeter seal area), preferably more than 40 g/m², but it can me even more than 100 g/m² or more. For processing and user acceptance reasons, the basis weight is preferably less than 500 g/m² or even not more than 300 g/m².

The perimeter seal may be positioned outwardly and separately of the absorbent core or the absorbent core and the perimeter seal may be overlapping or even integrally formed. Also, a portion of the perimeter seal may be positioned outwardly of the core, e.g., laterally outwardly, whilst another portion of the perimeter seal may be positioned inside the perimeter of the absorbent core, e.g., at the longitudinal ends. The perimeter seal may also coincide with the perimeter of the absorbent mat.

If the absorbent core extends into or possibly also beyond the perimeter seal, the total amount of SAP in the perimeter seal should be at least 5% more, preferably 10% or even more as compared to the amount of SAP in the neighborhood of the perimeter seal. In these cases, the amount of SAP in the perimeter seal may be expressed as "amount of core SAP in perimeter seal", "amount of perimeter seal SAP in the perimeter seal", and "total amount of SAP in the perimeter seal".

The SAP material in the perimeter seal may be the same or different type as the SAP in the absorbent core, if present. In order to provide the sealing function, the SAP preferably does not exhibit a high permeability, and SFC values may be less than $20 \times 10^{-7}$ cm³ sec/g, or even as low as $4 \times 10^{-7}$ cm³ sec/g, but should not exceed $60 \times 10^{-7}$ cm³ sec/g, whereby SFC refers to saline flow conductivity as may be determined according to the method as described in detail in U.S. Pat. No. 5,599,335, to which express reference is made for this test method. The SAP materials may also or alternatively exhibit a smaller particle size distribution, and thus comprise more than 10%, more than 30% or even more than 50% of particles exhibiting a particle size of 150 µm or less, as may be determined by EDANA NWSP220.0.R2 or equivalent.

The SAP in the perimeter seal may be positioned z-directionally in various options.

In a first and preferred option, the absorbent core is made as two sublayers and the SAP for the perimeter seal may be positioned between the two sublayers of the absorbent core. Such a positioning may be accomplished by method as generally known in the art, with so called "SAP-printing" being a preferred execution. Whilst some of the applied SAP may penetrate into the absorbent layers, more pronounced into the one onto which the SAP particles have been positioned, the particles may also form a zone of essentially pure SAP particles (i.e. no fibers there between), which may provide a "gel blocking layer".

Another option provides an increased local SAP particle basis weight when forming a single layer of an absorbent core. Yet in a further option the SAP particles are positioned between core cover materials that extend outwardly of the absorbent core.

It is also contemplated that the SAP materials is applied in a non-particular form, such as when SAP fibers, optionally in a ribbon form, are introduced. Although less preferred, a further option includes in-situ polymerization of monomers that may be applied in liquid form.

The composite of the absorbent core and the perimeter seal may further be consolidated by embossing, as described for the absorbent core in the above. Upon combining the composite with the cover materials, the absorbent mat is formed, which may be connected by adhesive or melt fusion connecting and which may be finished such as by folding and cutting.

The overall process according to the present invention for the manufacturing of an absorbent mat comprises a core making section, as may be the providing of preformed cores such as from unwinding from a roll or spool or pulling out of a box ("festooning"). Often it may be preferred to form the absorbent cores in-line. To this end, the core making section comprises at least one fiber supply system, preferably a supply system for individualized cellulosic pulp fibers, and optionally a core SAP supply system. Optionally, one or more core carrier(s) such as tissue(s) may be provided from the core carrier supply(ies). The perimeter seal SAP may be supplied from a perimeter seal SAP supply, which may be completely separate from the core SAP system, or share at least some equipment elements. The perimeter seal may then be formed concurrently with the forming of the absorbent core, or it may be added after the forming of the absorbent core, or even prior to that, e.g. by placing the perimeter seal SAP onto a carrier, which is then combined with the absorbent core materials.

Before combining the composite comprising the absorbent core and the perimeter seal with the cover materials, the composite may be further treated such as by being compressed such as by calendering, the continuous webs may be separated, such as by cutting, and consecutive absorbent cores may be spaced apart from each other.

Once the absorbent cores are spaced apart, the absorbent mat may be assembled in a mat making unit, wherein the first and second mat cover materials are provided from supply units, and the composite with the absorbent core and the perimeter seal and the mat cover materials may be appropriately connected, such as by glue application, compression, or melt fusion sealing such as heat sealing, heat or pressure bonding or ultrasonic bonding. Having thusly described the present invention in general terms, specific aspects are now explained in more detail by referring to the accompanying figures. It should, however be noted, that this description should not be seen limiting, and individual elements or features described in the context of one exemplary execution may be combined with individual elements or features of another exemplary execution.

In FIG. 1A with a perspective view the general set-up for an absorbent mat 1000 is exemplarily depicted. In FIG. 1A, the support structure 100 may be a bed or a bed mattress.

FIG. 1B and FIG. 1C show schematically cross-sectional views and FIG. 1D a top view of an absorbent mat. The mat can be described in a Cartesian coordinate system with

- a first extension 104, in the x-direction, corresponding to the length of the mat and defining generally longitudinally extending mat margins;
- a second extension 106, in the y-direction, corresponding to width of the mat, preferably being shorter said first extension, and defining generally cross-directionally extending mat margins; and
- a third extension 105 in the z-direction, corresponding to the thickness of the mat, perpendicular to the first and the second extensions, and significantly smaller than said first and said second extension.

The absorbent mat 1000 exhibits a first surface 1010 that may be oriented towards a user on said mat (not shown) and may be part of a first cover web 1300, as may be referred to as a topsheet. Opposite thereof is a second cover 1400, as may be referred to as backsheet with a second surface 1020. The first and the second cover may be connected at the perimeter of the absorbent mat, such as by a perimeter connection 1510. The absorbent mat comprises longitudinally (1040) and cross-directionally (1060) extending margins. Positioned between the first and the second cover is an absorbent core 1100, which may comprise fibers, such as cellulosic fibers, and also may comprise SAP particles, e.g. intermixed therein. The absorbent core may be connected to the cover webs 1300 and 1400 such as by an adhesive as indicated by 1520. The absorbent mat further comprises a perimeter seal 1200, as may be embedded in the absorbent core, such as by an increased SAP concentration.

Figure 2:
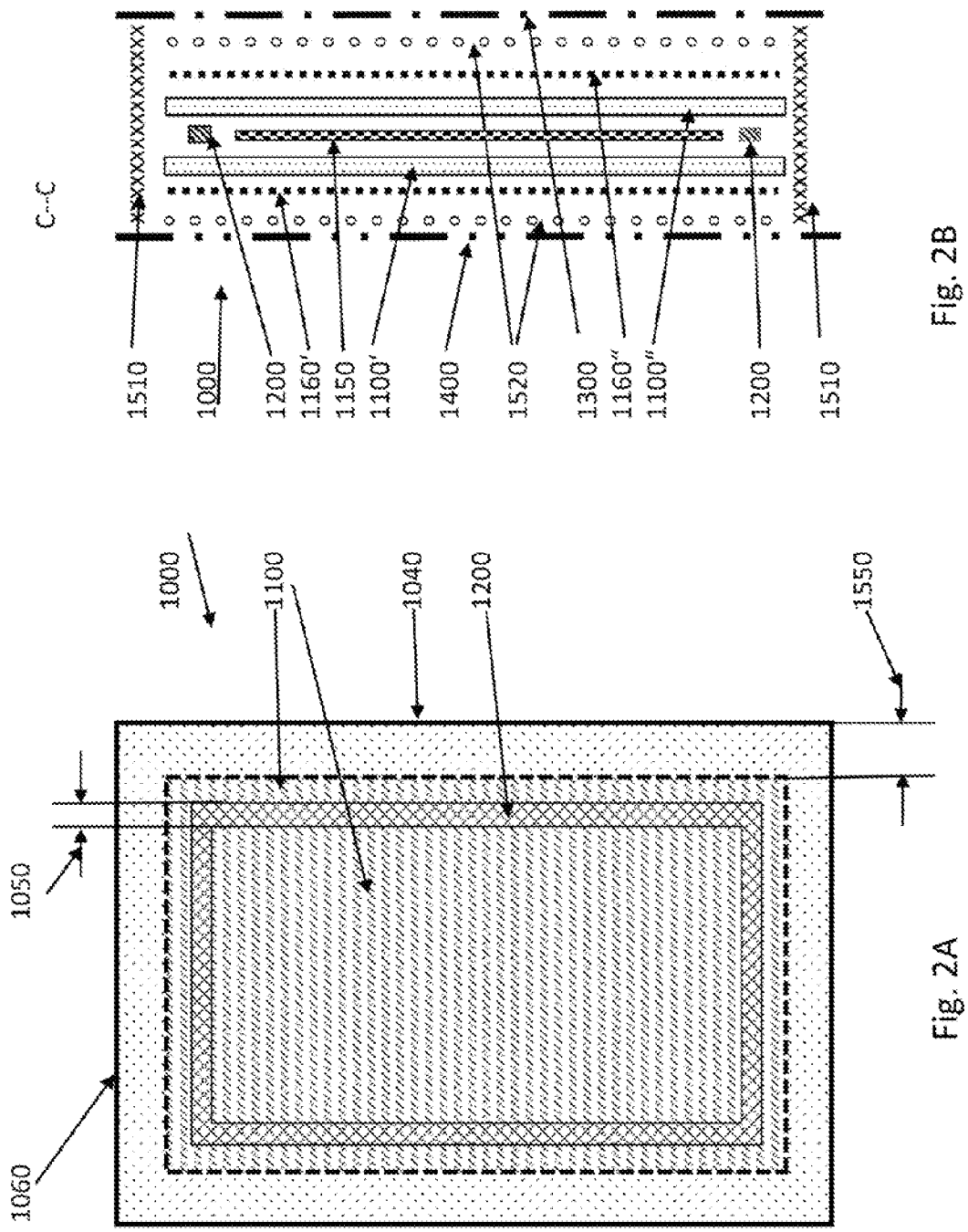
FIGS. 2A and B depict an absorbent mat according to the present invention with certain particular elements and features.

In FIG. 2A in a top view and FIG. 2B in a cross-sectional view further particular elements of the absorbent mat 1000 are depicted. The absorbent mat 1000 is shown with an absorbent core 1100, both in a rectangular shape, and the core being x-y-directionally distanced from the absorbent mat margins 1040 and 1060 by a mat perimeter width 1550. The perimeter seal 1200 is shown to be positioned inside the absorbent core, exhibiting a perimeter seal width 1050. As can be seen in FIG. 2B, the absorbent core comprises two sublayers 1100' and 1100", as may be pure cellulosic layers, between which a layer of core SAP particles 1150 is positioned. The perimeter seal 1200 comprises SAP particles, as may be positioned between the sublayers 1100' and 1100" at higher basis weights than the core layer SAP 1150.

Figure 3:
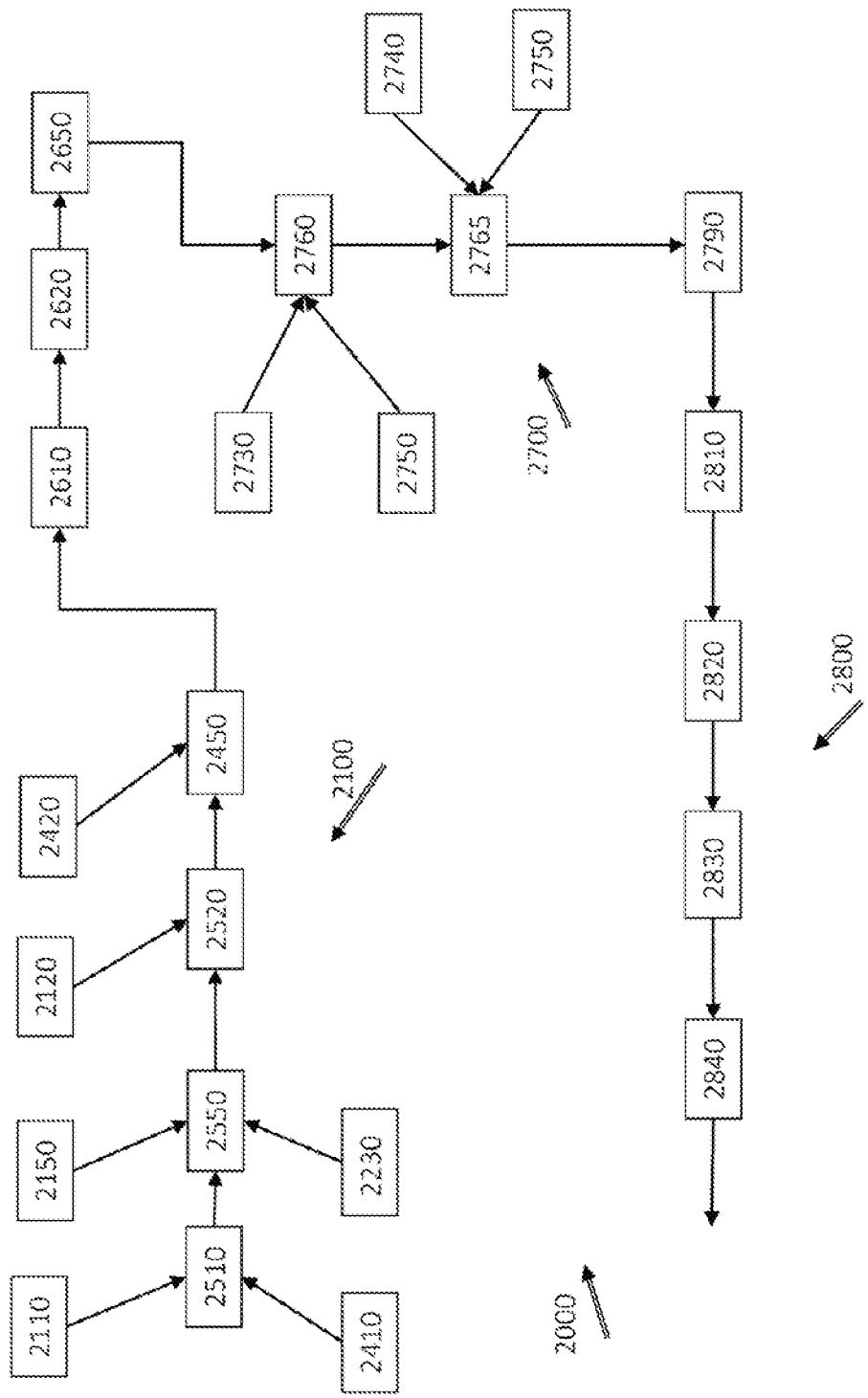
FIG. 3 depicts a schematic flow chart for a process according to the present invention.

FIG. 3 depicts schematically the process elements as may be combined to produce an absorbent mat according to the present invention. Pleases note, that certain elements are optional or even alternative to certain other elements, as described in the above when referring to FIGS. 1 and 2.

The overall process 2000 for manufacturing the absorbent mat comprises a composite making section 2100 for forming the absorbent core and applying the perimeter seal. This may include the providing of preformed cores such as from unwinding from a roll or spool or pulling out of a box ("festooning"). However, for logistic and/or economic reasons it may be preferred to form the absorbent core 1100 in-line.

To this end, the composite making section comprises at least one fiber, preferably cellulosic pulp, supply system and optionally a SAP supply system. In a preferred execution, pulp is supplied from two pulp supply systems 2110 and 2120 and laid down in two subsequent lay-down steps 2510 and 2520 to form absorbent core layers 1100' and 1100". Optionally a first core carrier as a tissue may be provided from a first core carrier supply 2410 to the first core lay-down step 2510. SAP from a core SAP supply system 2150 may be may be positioned between the two pulp lay-down steps 2510 and 2520 in a core SAP addition step 2550. The perimeter seal SAP may be supplied from a perimeter seal SAP supply 2230 and be added to the absorbent core at the perimeter seal addition step. This step 2350 can be between the lay-down of the pulp, and may be prior to, simultaneously with or after the core SAP addition, in the figure indicated to be simultaneous. Once the absorbent core with the perimeter seal is formed, a second core carrier such as a tissue, may be provided from a second core carrier supply 2420 after the second core lay-down step 2520 in the second carrier infeed step 2450.

FIGS. 4A and B depict schematically two snapshots of the manufacturing process, showing sequences of absorbent cores 1100, 1100" with a perimeter seal 1200' and 1200" applied thereto.

In FIG. 4A the option is depicted, where the absorbent cores 1100', 1100" are longitudinally spaced apart, and positioned on a core carrier, 1160, such as a tissue.

In FIG. 4B, the option is depicted, where subsequent absorbent cores are not spaced apart, and the perimeter seal may be formed as a stripe of double width, which may be separated in the core separation step 2620

Referring to FIG. 3 again, the combined composite may now be compressed such as in an embossing step 2610, further cut to the desired length in a separation step 2620 and longitudinally spaced apart in a re-pitching step 2650. If at least one tissue is present, this re-pitching may be by simple pull action e.g. between transfer rolls or belts. In case of no tissues being present and the absorbent core exhibiting a low strength, the repitching may be achieved by known repitch tools, such as repitch wheels.

Once the absorbent cores are spaced apart, the absorbent mat may be assembled in a mat making unit 2700, wherein the first and second mat cover materials are provided from supply units 2730 and 2740, respectively. Adhesives may be provided 2750 and applied in the respective combining units 2760 and 2765 where the cover webs and the absorbent core are combined. The connecting of the composite and the cover may be accomplished or further strengthened in a connecting unit 2790, as may be a compression unit like an embossing or calendering roll unit, or a melt fusion unit such as heat sealing, heat or pressure bonding or ultrasonic bonding units, or a combination of such units.

In the mat finishing steps 2800, the mat may be longitudinally folded 2810, separated to the final length 2820, final folded 2830 and packed 2840 for being distributed to an end user.

The invention claimed is:

1. A disposable absorbent mat exhibiting in Cartesian coordinates
    a first extension in the x-direction, corresponding to a length of the mat and defining generally x-directionally extending mat margins;
    a second extension in the y-direction, corresponding to a width of the mat, the second extension being shorter said first extension, and defining generally cross-directionally extending mat margins;
    a third extension in the z-direction, corresponding to the thickness of the mat, perpendicular to said first and said second extensions, and smaller than said first and said second extension;
    said absorbent mat comprising z-directionally
    a first surface of a first cover web adapted for being oriented towards a user;
    a second surface of a second cover web, opposite said first surface and adapted for being oriented towards a support; and
    an absorbent core between the first and the second surface, comprising fibrous material, said absorbent core being x-y directionally distanced from said mat margins, and a superabsorbent polymer (SAP) material at an essentially x-y-directional homogeneous distribution, and
    at least one core carrier web material;
    said first and said second cover web extending longitudinally and laterally outwardly of said absorbent core, thereby forming a mat perimeter between said mat margins and said absorbent core x- and y-directionally, and being connected to each other in said mat perimeter at a perimeter connection,
    said absorbent mat further comprising a perimeter seal, said perimeter seal being positioned inwardly from said perimeter connection and being positioned along a perimeter seal line within the x-y-extending margins of the absorbent mat, and having a perimeter seal width extending perpendicular to the perimeter seal line of at least 5 mm; and
    said perimeter seal comprising a superabsorbent polymer (SAP) material, at a local basis weight concentration of at least 60% of a combined basis weight of fibers, the fibers comprising cellulose fibers, total SAP, and the core carrier web material, and the local basis weight being a ratio of at least 1.05 times, preferably more than 1.10 times as high as a basis weight of the SAP in said absorbent core.

2. An absorbent mat according to claim 1, further exhibiting one or more of the features selected from the group consisting of:
    i) said perimeter seal width is essentially constant along said perimeter seal line;
    ii) the SAP is applied to the perimeter seal at a local basis weight of more than 25 g/m$^2$, preferably more than 100 g/m$^2$, even more preferably more than 300 g/m$^2$;
    iii) said local basis weight concentration in the perimeter seal is essentially constant along said perimeter seal line;
    iv) said absorbent core comprises SAP material at a basis weight of less than about 300 g/m$^2$ preferably less than 100 g/m$^2$, more preferably less than 50 g/m$^2$, whereby said SAP material is either essentially homogeneously distributed in a x-y-plane, or said basis weight of said SAP material is an average of the area encircled by said perimeter seal line;
    v) said perimeter seal comprises SAP material which exhibits an saline flow conductivity (SFC) value of less than about $40 \times 10^{-7}$ cm$^3$ sec/g;
    vi) said absorbent core extends laterally or longitudinally outwardly of said perimeter seal;
    vii) said perimeter seal follows essentially the shape of said mat perimeter;
    viii) the distance between said perimeter seal and said mat perimeter is, when measured perpendicularly to said perimeter seal line, less than about 100 mm, preferably less than 50 mm,
    ix) said perimeter seal line has an oval or a rectangular shape, the rectangular shape optionally formed with rounded corners.

3. A method for the manufacture of an absorbent mat said absorbent mat exhibiting in Cartesian coordinates
    a first extension in the x-direction, corresponding to a length of the mat and corresponding to a machine direction of the manufacturing method;
    a second extension in the y-direction, corresponding to a width of the mat, the second extension being shorter said first extension and corresponding to a cross-machine direction of the manufacturing method;

a third extension, z-direction or thickness, perpendicular to said first and said second extensions, and smaller than said first and said second extension; said absorbent mat comprising z-directionally a first surface of a first cover web adapted for being oriented towards a user;

a second surface of a second cover web opposite said first surface and adapted for being oriented towards a support, an absorbent core between the first and second surface, exhibiting an absorbent core margin and an x-y-extension smaller than the x-y-extension of said mat, and comprising fibrous material, and a superabsorbent polymer (SAP), said first and said second cover web extending longitudinally and laterally outwardly of said absorbent core, thereby forming a mat perimeter circumscribing said core x- and y-directionally, and being connected to each other in said perimeter at a perimeter connection, said absorbent mat further optionally comprising at least a first core wrap material; and further comprising a perimeter seal, said perimeter seal being positioned inwardly from said perimeter connection and exhibiting a perimeter seal width extending perpendicular to the perimeter seal line of at least 5 mm;

and being positioned along a closed perimeter seal line within the x-y-extending margins of the absorbent mat, and said perimeter seal comprising a superabsorbent material, at a local basis weight concentration of at least 60% of a combined basis weight of fibers, the fibers comprising cellulose fibers, SAP, and a core carrier web material, and wherein said SAP is applied at a local basis weight being a ratio of at least 1.05 times, preferably more than 1.10 times as high as a basis weight of the SAP in said absorbent core, said method comprising the steps of a) providing
   a1) a first and a second cover web material from a web supply unit, respectively;
   a2) an absorbent core making unit, selected from a fiber lay-down unit for individualizing fibers and forming a web of fibers, wherein said fibers are cellulose fibers, and/or a core web unwinding unit;
   a3) a core wrap supply unit, or a tissue unwind unit;
   a4) at least one superabsorbent material supply and application unit;
   a5) at least one connecting unit;
b) making an absorbent core with said core making unit and a SAP supply and application unit;
c) forming a perimeter seal before, during, or after making of the absorbent core such that said perimeter seal is exhibiting a perimeter seal width extending perpendicular to the perimeter seal line of at least 5 mm; and is positioned along a closed perimeter seal line; and comprising superabsorbent material, at a local basis weight concentration of at least 60% of the combined basis weight of cellulose, SAP, and core carrier, if present, and at a local basis weight that is at least 1.05;
d) enveloping said absorbent core and said perimeter seal between said first and said second cover web;
e) connecting said first and second cover webs at least in said mat perimeter outwardly of said perimeter seal, and optionally said core wrap materials to said absorbent core; and optionally said core wrap material(s) to said first and second cover webs.

4. A method for the manufacture of an absorbent mat according to claim 3, wherein said perimeter seal is formed by SAP printing, preferably without simultaneously applying pulp fibers to said perimeter seal.

5. A method for the manufacture of an absorbent mat according to claim 3, wherein said connecting is performed by glue application, preferably spray glue application or melt fusion bonding, preferably ultrasonic bonding.

6. The absorbent mat according to claim 1, wherein the fibrous material of the absorbent core is cellulosic material.

7. The absorbent mat according to claim 1, wherein the core carrier web material is a paper tissue material.

8. The absorbent mat according to claim 1, wherein the perimeter seal width is more than 10 mm and less than 40 mm.

9. The absorbent mat according to claim 8, wherein the perimeter seal width is more than 10 mm and less than 30 mm.

10. A method for the manufacture of an absorbent mat according to claim 3, wherein the fibrous material of the absorbent core is cellulosic material.

11. A method for the manufacture of an absorbent mat according to claim 3, wherein the perimeter seal width is more than 10 mm and less than 40 mm.

12. A method for the manufacture of an absorbent mat according to claim 3, wherein the perimeter seal width is more than 10 mm and less than 30 mm.

13. A method for the manufacture of an absorbent mat according to claim 3, wherein the step of forming a perimeter seal before, during, or after making of the absorbent core such that said perimeter seal is exhibiting a perimeter seal width extending perpendicular to the perimeter seal line of more than 10 mm and less than 40 mm.

14. A method for the manufacture of an absorbent mat according to claim 13, wherein the step of forming a perimeter seal before, during, or after making of the absorbent core such that said perimeter seal is exhibiting a perimeter seal width extending perpendicular to the perimeter seal line of more than 10 mm and less than 30 mm.

* * * * *